US00PP16898P3

(12) United States Plant Patent
Rubio

(10) Patent No.: US PP16,898 P3
(45) Date of Patent: Aug. 1, 2006

(54) STRAWBERRY PLANT NAMED 'MACARENA'

(50) Latin Name: *Fragaria×ananassa*
Varietal Denomination: Macarena

(75) Inventor: Ignacio Abascal Rubio, Navarra (ES)

(73) Assignee: Plantas de Navarra S.A., Valtierra (ES)

( * ) Notice: Subject to any disclaimer, the term of this patent is extended or adjusted under 35 U.S.C. 154(b) by 105 days.

(21) Appl. No.: 10/678,852

(22) Filed: Oct. 2, 2003

(65) Prior Publication Data

US 2005/0010983 P1 Jan. 13, 2005

(30) Foreign Application Priority Data

Jul. 7, 2003 (EP) ..... 2003/1230

(51) Int. Cl.
*A01H 5/00* (2006.01)

(52) U.S. Cl. ..... Plt./208

(58) Field of Classification Search ..... Plt./208
See application file for complete search history.

(56) References Cited

PUBLICATIONS

UPOV.ROM, 0018NV/1392, Feb. 20, 1992, 'Linda', grant Dec. 30, 1994.*

* cited by examiner

*Primary Examiner*—Anne Marie Grunberg
(74) *Attorney, Agent, or Firm*—Christie, Parker & Hale, LLP

(57) ABSTRACT

Described is a strawberry variety having very early time of ripening and abundant production of orange red colored, conical shaped, and firm fruit; and large fruit size.

9 Drawing Sheets

Classification: The present invention relates to a new *Fragaria×ananassa* Duch. plant.

Variety denomination: The new plant has the varietal denomination of 'Macarena'.

BACKGROUND OF THE INVENTION

The new variety of strawberry was created in a breeding program by crossing two parents; in particular, by crossing as seed parent an undistributed strawberry parent designated 88-033 (unpatented) and as pollen parent an undistributed strawberry parent designated 9150 (unpatented). Female is a component of a parent collection, from a selection made between plants issued from seeds in a free pollination in a population of different origin. Male is a selection from breeder's program of Planasa. Both parental varieties are proprietary and have not been commercialized, distributed or patented.

The resulting seedling of the new variety was grown and asexually propagated by runners in Soria, Spain, 3°W., 41°N., 3000 feet elevation. Clones of the new variety were further asexually propagated and extensively tested. This propagation and testing has demonstrated that the combination of traits disclosed herein which characterize the new variety are fixed and retained true to type through successive generations of asexual reproduction.

SUMMARY OF THE INVENTION

The present invention relates to a new and distinct strawberry variety. The varietal denomination of the new variety is 'Macarena'. Among the characteristics which appear to distinguish the new variety from other varieties are a combination of traits which include plant vigor and density that appear medium and very early time of ripening (50% of plants with ripe fruits) and abundant production of orange red colored, conical shaped, and firm fruit; and large fruit size.

COMPARISON TO PARENTS

1. Seed parent 88-033 (unpatented) shows a dark red fruit color (RHS red group near 47B to 47A), whereas in 'Macarena' it is an orange red fruit color (RHS orange-red near 34B to 34A).
2. Fruit of seed parent 88-033 shows an almost cylindrical to conical shape. In 'Macarena' it is conical.
3. 'Macarena' shows a fruit size larger than seed parent 88-033 or pollen parent 9150 (unpatented).
4. Precocity in seed parent 86-032 and in pollen parent 9150 is less than in 'Macarena'.

COMPARISON TO CLOSEST VARIETY

The new variety is closest to the variety 'Camarosa' (U.S. Plant Pat. No. 8,708), but is distinguished therefrom by the following characteristics possessed by 'Macarena' which are different than, or not possessed by, 'Camarosa'.

1. 'Camarosa' (U.S. Plant Pat. No. 8,708) exhibits a plant habit globose whereas 'Macarena' exhibits a plant habit flat to flat globose.
2. 'Camarosa' (U.S. Plant Pat. No. 8,708) shows fruits with a ratio of length/width slightly longer than broad, whereas 'Macarena' shows fruits with a ratio length/width much longer than broad.
3. 'Camarosa' (U.S. Plant Pat. No. 8,708) shows an almost cylindrical shape. In 'Macarena' it is conical.
4. 'Camarosa' (U.S. Plant Pat. No. 8,708) shows a fruit size more large than 'Macarena'.
5. The insertion of achenes in 'Camarosa' (U.S. Plant Pat. No. 8,708) is level with surface of fruit, whereas in 'Macarena' is below surface.
6. 'Camarosa' (U.S. Plant Pat. No. 8,708) shows a dark red fruit color (RHS red group near 47B to 47A), whereas in 'Macarena' it is an orange red fruit color (RHS orange-red near 34B to 34A).

7. 'Camarosa' (U.S. Plant Pat. No. 8,708) shows a dark red flesh color (RHS red group near to 42A), whereas in 'Macarena' it is light red flesh color (RHS red group near 40D to 40C).

The differences in the fruits of 'Camarosa' (U.S. Plant Pat. No. 8,708) and the new variety are shown in FIGS. 6 and 7, and FIGS. 8 and 9. These differences are maintained during the harvest season.

8. Time of ripening (50% of plants with ripe fruits) in 'Macarena' is more early than in 'Camarosa' (U.S. Plant Pat. No. 8,708).

BRIEF DESCRIPTION OF THE ILLUSTRATIONS

The accompanying photographs show typical specimens of the new variety, designated 98.51.123 in the illustrations, including fruit, foliage and flower, in color as nearly true as it is reasonably possible to make in color illustrations of this character.

The plants depicted in the drawings were planted Oct. 30, 2002 in the farm of La Mogalla in Cartaya (Huelva), Spain, about 7°W, 37°N, 45 feet elevation.

Drawings were taken April, 2003 (about Apr. 15, 2003): minimum temperate about 16 to 18° Centigrade, maximum temperate about 31 to 33° Centigrade.

Figure 1:
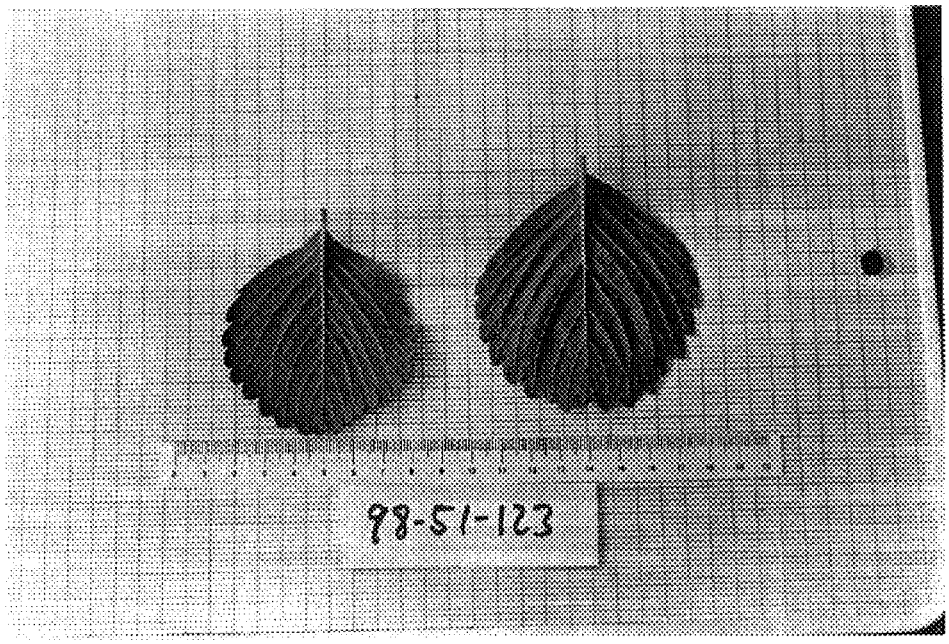
FIG. 1 shows the undersurface of a typical terminal leaflet of the new variety (designated 98.51.123), with a shape of base obtuse and in which the length/width ratio is longer than broad.
Figure 2:
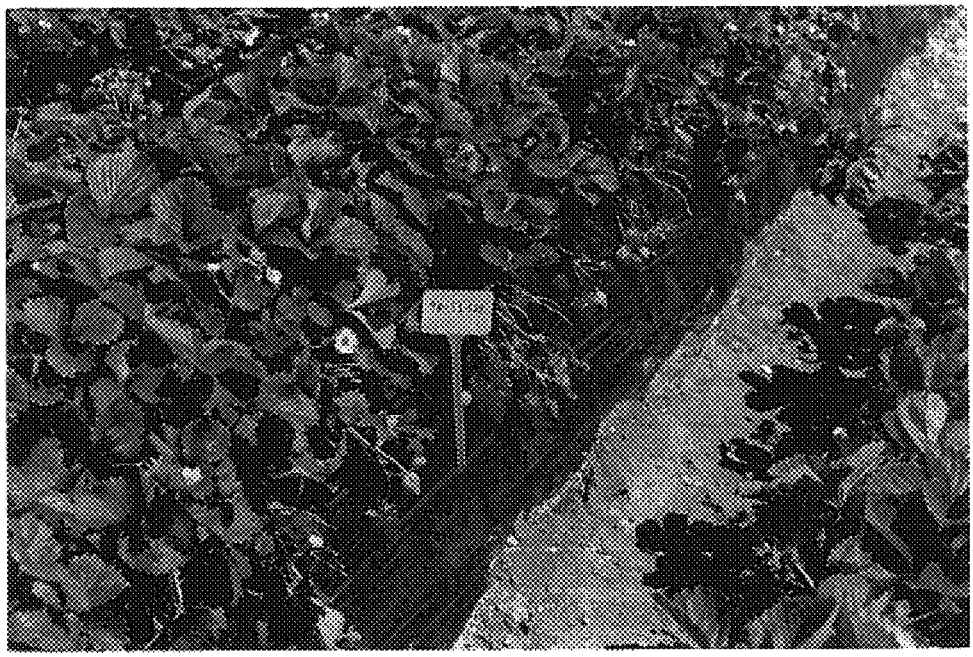
FIG. 2 and FIG. 3 show the fruit against a background of the top surface of the foliage of the new variety (designated 98.51.123).
Figure 3:
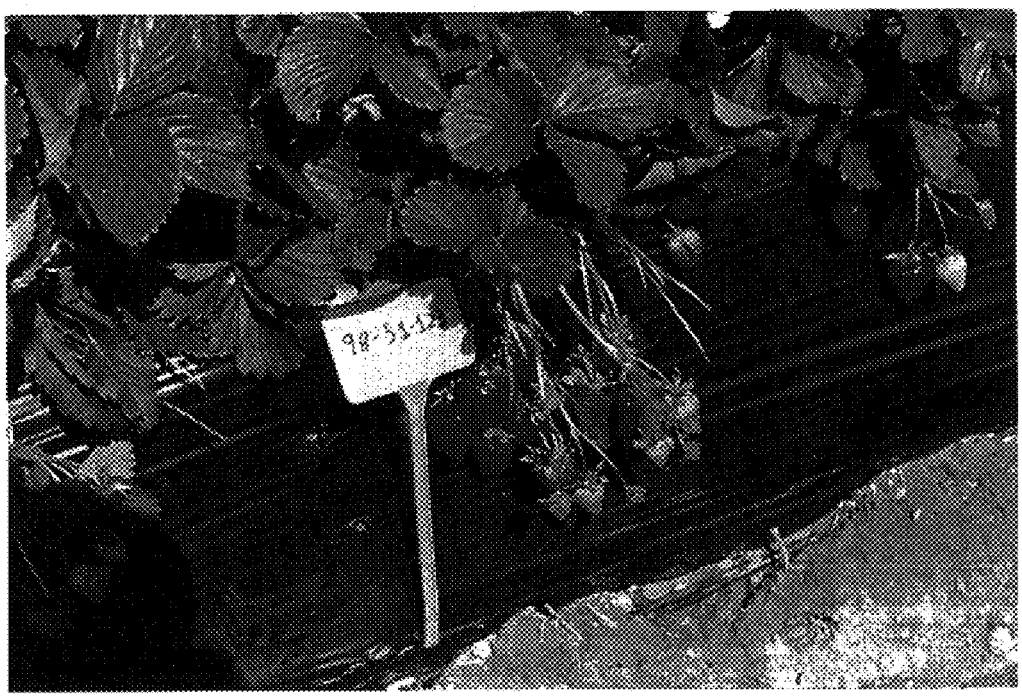
Figure 4:
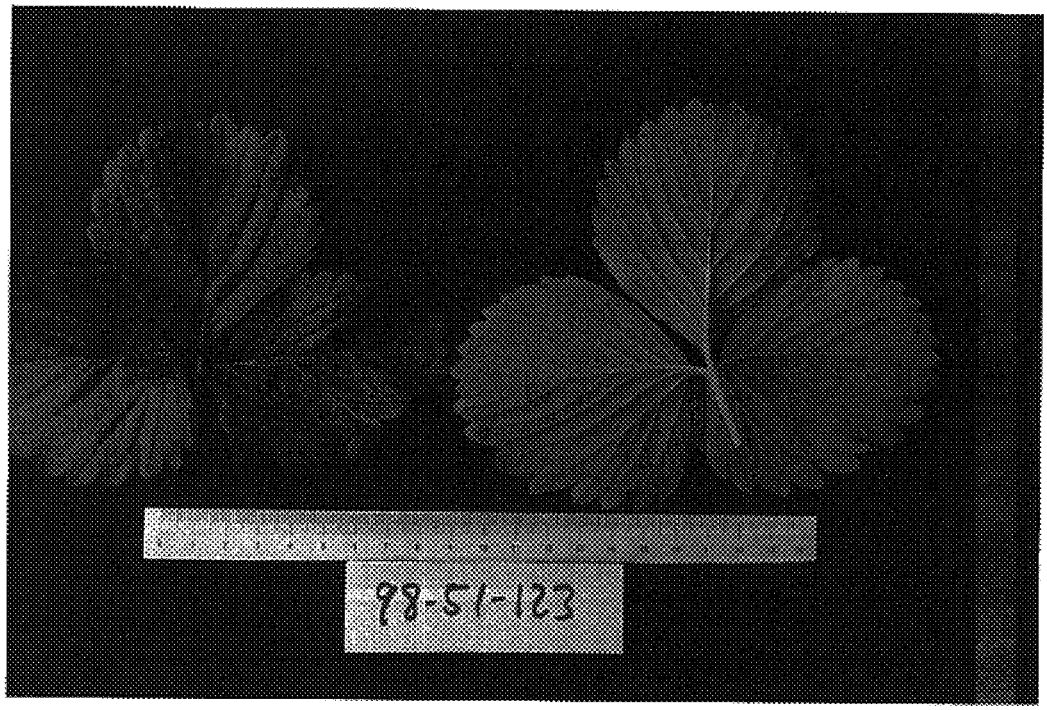
FIG. 4 shows the top and undersurface of a complete leave of the new variety (designated 98.51.123) in which we can see that the leaf color of upperside (RHS green group near 131C to 131B) and of underside (RHS green group near 138C to 138B).
Figure 5:
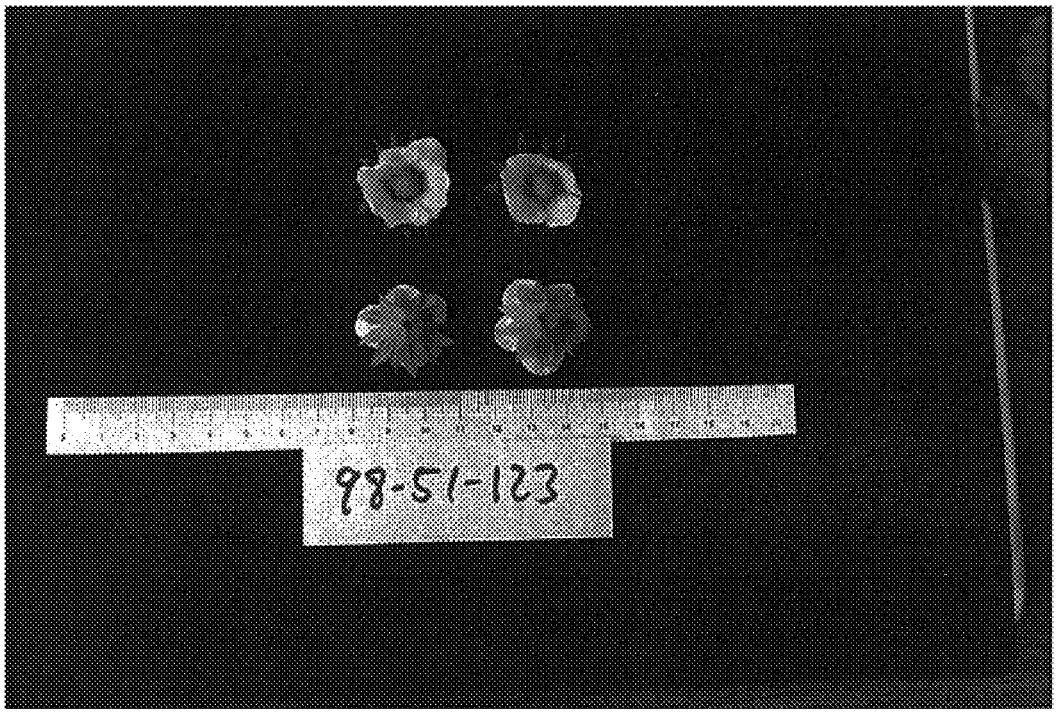
FIG. 5 shows the flower and reproductive organs of the new variety (designated 98.51.123).
Figure 6:
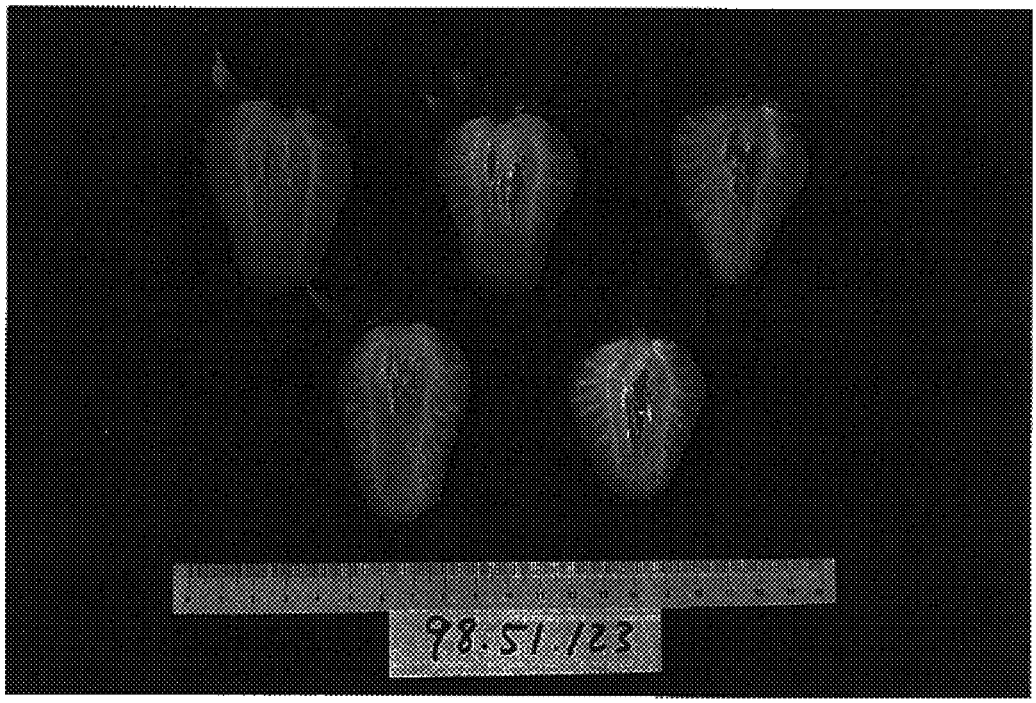
FIG. 6 shows typical fruits of the new variety (designated 98.51.123) in cross section illustrating the typical flesh and flesh coloration, conspicuous core and core cavity and conical shape, fruit size, and fruit ratio length/width much longer than broad.
Figure 7:
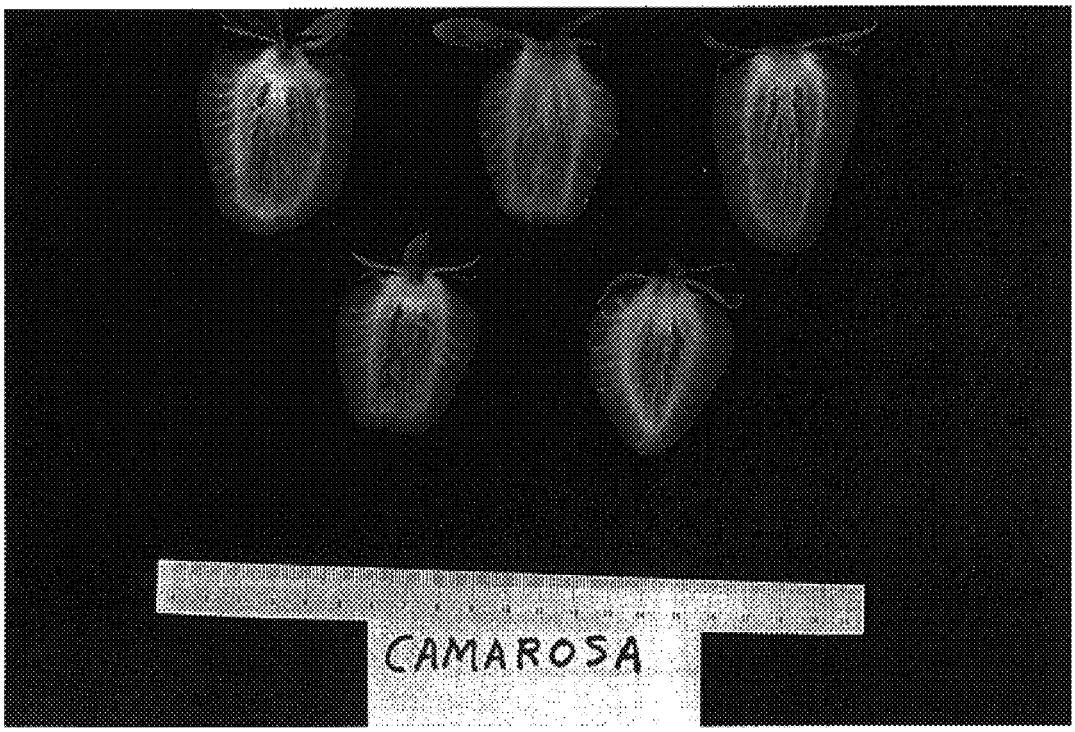

FIG. 7 shows typical fruits of the 'Camarosa' (U.S. Plant Pat. No. 8,708) in cross-section illustrating the typical flesh and flesh coloration, conspicuous core and core cavity and almost cylindrical shape, fruit size, and fruit ratio length/width slightly longer than broad.

Figure 8:
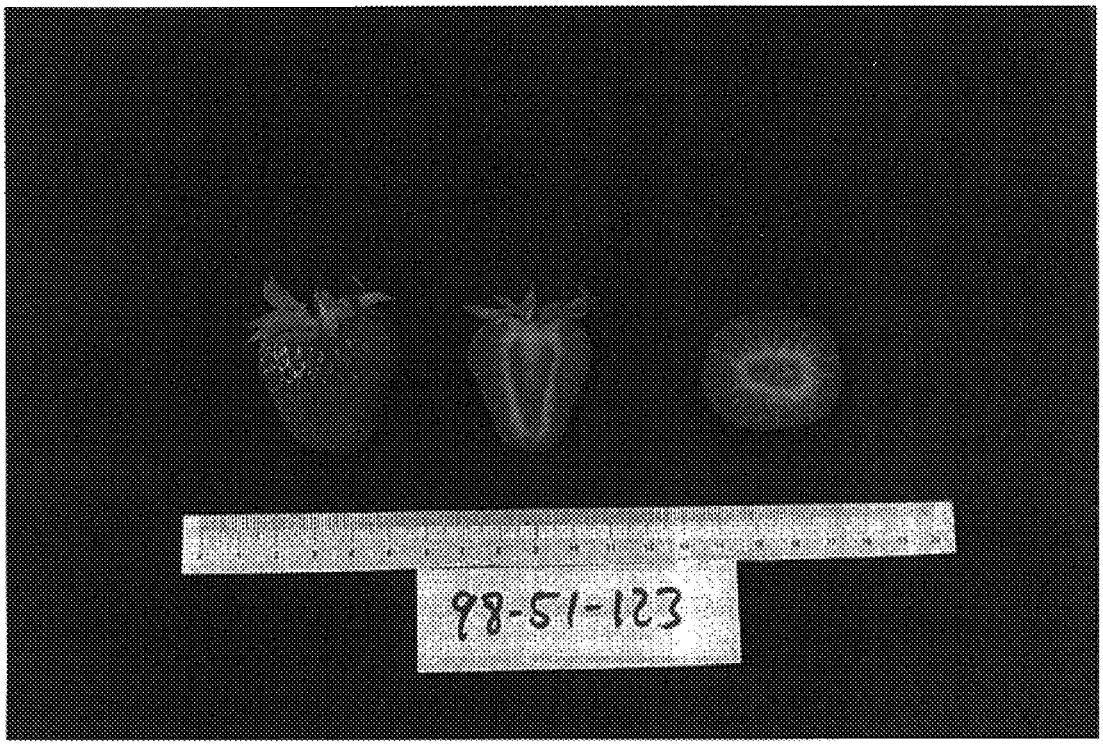

FIG. 8 shows whole and sliced, detached fruit of the new variety (designated 98.51.123) with the typical orange red fruit color, and the light red flesh color.

Figure 9:
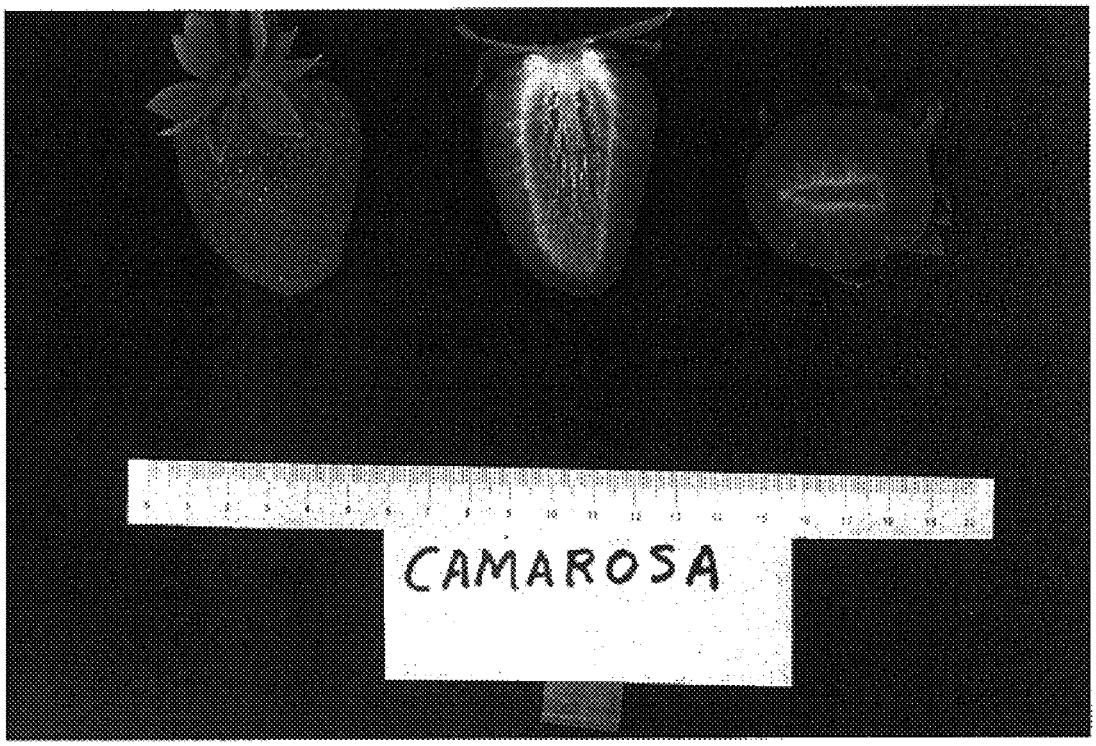

FIG. 9 shows whole and sliced, detached fruit of the 'Camarosa' (U.S. Plant Pat. No. 8,708) with the typical dark red fruit color, and the dark red flesh color.

DETAILED DESCRIPTION OF THE NEW VARIETY

The following detailed description of the new variety is based upon observations taken of plants and fruits grown "underglass", i.e,. undertunnel, in the farm of La Mogalla in Cartaya (Huelva), Spain, 7°W., 37°N., 45 feet elevation.

The following description is in accordance with UPOV terminology and the color terminology herein is in accordance with The Royal Horticultural Society Colour Chart (R.H.S.C.C.). The color descriptions and other phenotypical descriptions may deviate from the stated values and descriptions depending upon variation in environmental, seasonal, climatic and cultural conditions.

PROPAGATION

The new variety is principally propagated by way of runners. Although propagation by runners is presently preferred, other know methods of propagating strawberry plants may be used. Strawberries root well after transplanting.

The term "blistering" used herein refers to the texture or rugosity or surface ondulation inherent to leaves and is generally a constant characteristic.

GENERAL

'Macarena' is a short day variety that needs an induction to flowering by chilling, such as occurs at a high elevation nursery (fresh plant) or with cold storage (referred to as a frigo). Usually a short time is sufficient. 'Macarena' is self-fertile. It produces large quantity of pollen throughout the seasons and pollination is generally good as there are very few malformed fruit.

Production: Plants described are from high elevation nursery. Description taken in Cartaya (Huelva), Spain of plants planted in October 2002.

Number of repetitions: 2.

Plants per repetition: 225.

Comparison with 'Camarosa' (U.S. Plant Pat. No. 8,708): The new variety is compared with 'Camarosa' (U.S. Plant Pat. No. 8,708) in FIG. 6 and FIG. 7, and FIG. 8 and FIG. 9.

Accumulated production of 1st quality fruit (g/plant)

| Variety | 21-Fb | 28-Mr | 25-Ap | 15-My |
|---|---|---|---|---|
| MILSEI | 12 | 98 | 451 | 802 |
| CAMAROSA | 15 | 96 | 519 | 1035 |
| TUDNEW | 23 | 102 | 481 | 936 |
| 'MACARENA' | 24 | 110 | 517 | 1029 |

| Variety | 1st + 2nd Quality Fruit | Total | Weight (g/fruit) |
|---|---|---|---|
| MILSEI | 802 + 109 | 911 | 22 – 21 |
| CAMAROSA | 1035 + 183 | 1218 | 24 – 23 |
| TUDNEW | 936 + 104 | 1040 | 24 – 23 |
| 'MACARENA' | 1029 + 114 | 1143 | 23 – 22 |

Production total, to 15 May, of First Quality Fruit (1st quality) and Second Quality Fruit (2nd quality) in g/plant

| Variety | 1st quality | 2nd quality | TOTAL (1st quality + 2nd quality) | % 2nd quality |
|---|---|---|---|---|
| MILSEI | 802 | 109 | 911 | 12 |
| CAMAROSA | 1035 | 183 | 1218 | 15 |
| TUDNEW | 936 | 104 | 1040 | 10 |
| 'MACARENA' | 1029 | 114 | 1143 | 10 |

$$\% \text{ 2nd quality} = \frac{\text{2nd quality}}{\text{TOTAL}} \times 100$$

Weight (g/fruit) at two dates: 28 March and 15 May

-continued

| WEIGHT (g/fruit) | 28 March | 15 May |
|---|---|---|
| MILSEI | 22 | 21 |
| CAMAROSA | 24 | 23 |
| TUDNEW | 24 | 23 |
| 'MACARENA' | 23 | 22 |

WEIGHT is shown as the average weight per fruit in First Quality Fruits.

| FRUIT ANALYSIS | CAMAROSA | (98.51.123) MILSEI | TUDNEW | 'MACARENA' |
|---|---|---|---|---|
| Firmness (KG) | 0.60 | 0.75 | 0.34 | 0.98 |
| Humidity & Volatile Matter (%) | 91.10 | 91.10 | 92.00 | 91.80 |
| Dry Matter (%) | 8.90 | 8.90 | 8.00 | 8.20 |
| PH (to20°) | 3.50 | 3.60 | 3.60 | 3.60 |
| Acidity as Anhydride Citric (%) | 1.10 | 1.00 | 1.00 | 1.00 |
| Soluble Solids (°Brix) | 7.90 | 7.90 | 7.20 | 6.70 |
| Maturity Index | 7.30 | 7.90 | 7.10 | 6.80 |
| Content in Ascorbic Acid (ppm) | 670 | 430 | 560 | 600 |
| Dominant Tonality (nm) | 495 | 500 | 500 | 500 |
| Luminosity: Transmittance to 460 nm | 11.10 | 49.10 | 20.90 | 41.30 |

The following definitions apply:
Firmness: It is the fruit's resistance to penetration measured in Kilograms (Kg). The measure given has been obtained by the penetrometer ROZE Mod. Arbelette, with a 50 mm2 section head.
Dry Matter: It is the weight of the residual left from the trituration of the fruit after the drying process at a temperature of 103° C. + 2° C. until reaching constant weight.

$$(\%)\ \text{Dry Matter} = \frac{\text{Weight Dry Matter}}{\text{Weight Fresh Matter}} \times 100$$

Humidity & Volatile Matter: Represents the content in volatile metters and water of the fruits.
(%) Humidity & Volatile Matter = 100 − % Dry Matter
Maturity Index: Relation between Soluble solids and Acidity as Anhydride Citric.

$$\text{Maturity Index} = \frac{\text{Soluble solids}}{\text{Acidity as Anhydride Citric}}$$

The following additional information is provided to further describe the new variety.

Variety: Marcarena. Breeder Ref. 98.51.123.
Classification: *Fragaria×ananassa* Duch.
Plant:
*Habit.*—Flat to flat globose.
*Density.*—Medium.
*Vigor.*—Medium.
*Height.*—About 15–17 cm.
*Width.*—About 22–24 cm.
Leaf:
*Upperside.*—RHS green group color (near 131C to 131B). Underside — green group color (near 138C to 138B).
*Length.*—About 12 cm.
*Width.*—About 11 cm.
*Cross-section.*—Slightly concave.
*Leaf surface ondulation or blistering.*—Medium.
*Number of leaflets.*—Three only.
Leaf stem characteristics:
*Color.*—RHS green group (near 138D).
*Position of hairs.*—Upwards.
*Length.*—About 10 cm.
Terminal leaflet:
*Length/width ratio.*—Longer than broad.
*Length.*—About 6.5 cm. to 7.5 cm.
*Width.*—About 6.5 cm. to 7.5 cm.
*Shape of base.*—Obtuse.
*Shape of teeth.*—Crenate.
Petiole:
*Position of hairs.*—Upwards.
*Length.*—About 10 cm.
Stipule:
*Anthocyanin coloration.*—Weak. RHS greyed red group (near 179C to 179B).
Stolons:
*Number.*—Medium, about 7.
*Thickness.*—Medium, about 3 mm.
*Pubescence.*—Medium.
*Color.*—RHS green group (near 142D to 138D).
Inflorescence:
*Position relative to foliage.*—Beneath.
Flower:
*Size.*—Medium.
*Size of calyx relative to corolla.*—Larger.
*Spacing of petals.*—Overlapping.
Flower characteristics:
*Diameter primary flowers.*—About 2.0–2.5 cm.
*Diameter secondary flowers.*—About 2.0 cm.
*Number of petals.*—Normally about 6. No significant fragrance.
*Time from bloom to mature fruit* (*in Huelva, Spain*).—About 35 to 40 days.
*Stamens.*—Numerous with pollen present, fertile and abundant Length — approximately 4 mm. Color — RHS white group (near 155D to 155C).
*Anthers.*—Generally average in size. Color — RHS yellow group (near 12C to 13 C). and darkening with advanced maturity.
*Pollen.*—Fertile and abundant. Color — RHS yellow orange group (near 15C to 15B).
*Pistils.*—Numerous, generally average in size. Color — RHS yellow group (near 12B to 13B).
Petal:
*Length/width ratio.*—As long as broad.
Fruiting truss:
*Attitude.*—Semi-erect.
Fruit:
*Ratio of length/maximum width.*—Much longer than broad.
*Color.*—RHS orange red group (near 34B to 34A).
*Peduncle length of inflorescence stem.*—Primary fruit about 9 cm to 11 cm, secondary fruit about 6 cm to 7 cm. Color RHS green group (near 138D).
Primary fruit:
*Length.*—About 5.5–6.0 cm.
*Width.*—About 4.0–4.5 cm.
Secondary fruit:
*Length.*—About 4.5–5 cm.
*Width.*—About 3.0–3.5 cm.
*Size.*—Large.
*Predominant shape.*—Conical.

*Difference in shapes between primary and secondary fruits.*—Marked.
*Band without achenes.*—Narrow.
*Color of achenes.*—RHS orange red group (near 32C to 32B).
*Unevenness of surface.*—Absent or very weak to weak.
*Evenness of color.*—Slightly uneven to even.
*Glossiness.*—Medium.
*Insertion of achenes.*—Below surface.
*Insertion of calyx.*—Above fruit.
*Pose of the calyx segments.*—Reflexed.
*Size of calyx in relation to fruit diameter.*—Much larger.
*Adherence of calyx.*—Very strong.
*Firmness.*—Firm.
*Color of flesh.*—RHS red group (near 40D to 40C); lightening toward center.
*Distribution of red color of flesh.*—Marginal and central.
*Hollow center.*—Absent or very weakly expressed.
*Sweetness.*—Strong.
*Acidity.*—Medium.
*Time of flowering (50% of plants at first flower).*—Early to very early.
*Time of ripening (50% of plants with ripe fruits).*—Early to very early.
*Type of bearing.*—Not remontant.
*Chilling.*—Weak.
*Planting date.*—Oct. 30, 2002.
*10% Flowering.*—Dec. 27, 2002.
*First mature fruits.*—Jan. 30, 2003.
*Maturity (15–20 gms/plant).*—Feb. 12, 2003.

Time of flowering data: Date of planting: Oct. 30, 2002 in the farm of La Mogalla, in Cartaya (Huelva), Spain, about 7°W, 37°N, 45 feet elevation. 10% flowering occurs about Dec. 27, 2002 with first mature fruit about Jan. 30, 2003 and maturity (15–20 g/plant) about Feb. 12, 2003.

Time of flowers (50% of plants at first flower): About Jan. 5, 2003.

Storage qualities: 'Macarena' fruit maintain their quality characteristics when keeping them in a frigo chamber at temperatures of about 2° C. during 48 hours. The fruit's color remains substantially the same.

Time of ripening: After planting as aforesaid, plants are grown in raised beds undertunnel (small tunnel with small holes in plastic walls). Water and fertilizer were applied through drip irrigation. Time of ripening (50% of plants with ripe fruit) is about Feb. 7, 2003. First mature fruit is about Jan. 30, 2003 and maturity (15–20 gms/plant) is about Feb. 12, 2003.

General: The growing period in Huelva, Spain, where the observations were made, is between about December, 10 and May,15 of each year, with a maximum production at about mid-April. 'Macarena' is a short variety that benefits from induction to flowering by chilling, usually a few hours are sufficient, preferably at temperatures of 7° C. or less. Normally, the minimum number of hours is accumulated in the field during several days.

Disease resistance: No particular sensitivity to any disease or parasite has been observed for 'Macarena'.

I claim:

1. A new and distinct strawberry plant of the variety substantially as shown and described.

* * * * *